United States Patent [19]
Nielson et al.

[11] Patent Number: 5,262,427
[45] Date of Patent: Nov. 16, 1993

[54] 3-SUBSTITUTED AND OPTIONALLY 1-SUBSTITUTED AZACYCLIC OR AZABICYCLIC COMPOUNDS, PHARMACEUTICAL COMPOSITIONS, THEREOF AND THEIR USE AS STIMULANTS OF COGNITIVE FUNCTIONS

[75] Inventors: Lone Nielson, Kobenhavn; Frank Wätjen, Vaerlose; Jens W. Kindtler, Kokkedal; Preben H. Olesen, Kobenhavn; Per Sauerberg, Valby, Denmark

[73] Assignee: Novo Nordisk A/S, Bagsvaerd, Denmark

[21] Appl. No.: 268,940

[22] Filed: Nov. 8, 1988

[30] Foreign Application Priority Data

Nov. 13, 1987 [DK] Denmark .............. 5952/87
Dec. 28, 1987 [DK] Denmark .............. 6870/87
Mar. 2, 1988 [DK] Denmark .............. 1102/88

[51] Int. Cl.$^5$ ............... C07D 413/04; A61K 31/41
[52] U.S. Cl. ................. 514/304; 514/305; 514/315; 514/326; 514/340; 546/124; 546/125; 546/133; 546/209; 546/246; 546/275; 546/277; 546/334
[58] Field of Search ......... 514/304, 305, 315, 326, 514/340; 546/124, 125, 133, 209, 246, 275, 277, 334

[56] References Cited

U.S. PATENT DOCUMENTS

| | | | |
|---|---|---|---|
| 3,265,692 | 8/1966 | Harsanyi et al. | 546/209 X |
| 4,144,343 | 3/1979 | Baldwin et al. | 546/277 X |
| 4,518,601 | 5/1985 | Kristiansen et al. | 546/277 X |
| 4,710,508 | 12/1987 | Bergmeier et al. | 546/334 X |
| 4,786,648 | 11/1988 | Bergmeier et al. | 546/334 X |
| 4,837,241 | 6/1989 | Jensen et al. | 514/326 X |
| 4,866,077 | 9/1989 | Bogeso et al. | 514/326 |
| 4,925,858 | 5/1990 | Bogeso et al. | 546/209 X |
| 4,927,837 | 5/1990 | Galliani et al. | 546/246 X |
| 4,933,353 | 6/1990 | Jensen et al. | 546/277 X |
| 4,937,239 | 6/1990 | Lauffer et al. | 546/133 X |
| 4,968,691 | 11/1990 | Orlek et al. | 546/133 X |

FOREIGN PATENT DOCUMENTS

| | | |
|---|---|---|
| 0239309 | 9/1987 | European Pat. Off. . |
| 0307141 | 9/1988 | European Pat. Off. . |
| 296721 | 12/1988 | European Pat. Off. ............ 546/277 |
| 323864 | 7/1989 | European Pat. Off. ............ 546/133 |
| 2213152 | 8/1989 | United Kingdom ............... 546/246 |

OTHER PUBLICATIONS

Tamura et al., *Chemical Abstracts*, vol. 84, No. 175159v (1976).
Wells et al., *Chemical Abstracts*, vol. 67, No. 99958m (1967).
Baker et al., *Chemical Abstracts*, vol. 109, No. 54780s (1988).
Beecham Group PLC, *Chemical Abstracts*, vol. 110, No. 115165q (1989).
Bergmeier et al., *Chemical Abstracts*, vol. 110, No. 57518u (1989).
Bogeso et al., *Chemical Abstracts*, vol. 110, No. 192831f (1989).
Galliani et al., *Chemical Abstracts*, vol. 108, No. 204502y (1988).
Mastafanova et al., *Chemical Abstracts*, vol. 64, No. 12642f (1966).
Saunders et al., *Chemical Abstracts*, vol. 111, No. 39157s (1989).

*Primary Examiner*—Mary C. Lee
*Assistant Examiner*—Fiona T. Powers
*Attorney, Agent, or Firm*—Steve T. Zelson; Elias J. Lambiris

[57] ABSTRACT

Azacyclic compounds selected from the group consisting of

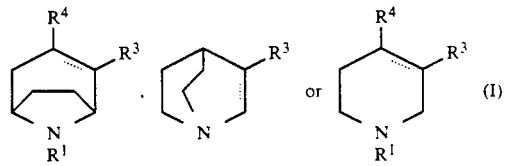

wherein
$R^1$ is H or $C_{1-6}$-alkyl (Abstract continued on next page.)

$R^3$ is

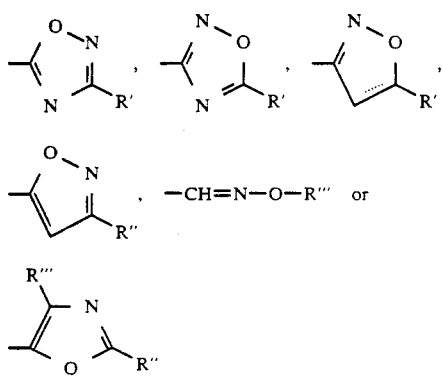

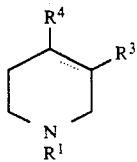 is $\overset{\diagdown}{\underset{\diagup}{HC}}-\overset{\diagdown}{\underset{\diagup}{CH}}$ or $\overset{\diagdown}{\diagup}C=C\overset{\diagup}{\diagdown}$ provided that $R^3$ is not

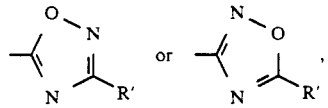

wherein R' is $C_{3-8}$-alkyl, cyclopropyl or $C_{1-3}$-alkoxymethyl, and provided that $R^3$ is not $-CH=N-OR'''$, wherein R''' is H or $C_{1-6}$-alkyl, when the compounds of formula I is

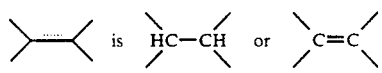

and a salt thereof with a pharmaceutically-acceptable acid.

wherein
R' is $C_{3-8}$-alkyl, cyclopropyl, $C_{4-8}$-cycloalkyl, benzyl which may be substituted, or $C_{1-4}$-alkoxy-$C_{1-4}$-alkyl, and
R'' is H or $C_{1-8}$-alkyl or $C_{1-6}$-alkoxy or $C_{1-4}$-alkoxy-$C_{1-4}$-alkyl or aryl, and
R''' is H or $C_{1-6}$-alkyl or $C_{4-8}$-cycloalkyl; and
$R^4$ is H, $C_{1-8}$-alkyl or Cl; and The new compounds are useful in improving the cognitive functions of the forebrain and hippocampus of mammals, and are useful in the treatment of Alzheimer's disease.

22 Claims, No Drawings

3-SUBSTITUTED AND OPTIONALLY 1-SUBSTITUTED AZACYCLIC OR AZABICYCLIC COMPOUNDS, PHARMACEUTICAL COMPOSITIONS, THEREOF AND THEIR USE AS STIMULANTS OF COGNITIVE FUNCTIONS

The present invention relates to therapeutically active azacyclic compounds, a method of preparing the same and to pharmaceutical compositions comprising the compounds. The novel compounds are useful as stimulants of the cognitive function of the forebrain and hippocampus of mammals and especially in the treatment of Alzheimer's disease.

Due to the in general improved health situation in the western world, elderly-related diseases are much more common now than in the past and are likely to be even more common in the future.

One of the elderly-related symptoms is a reduction of the cognitive functions. This symptom is especially pronounced in the patophysiological disease known as Alzheimer's disease. This disease is combined with, and also most likely caused by, a up to 90% degeneration of the muscarinic cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, then the postsynaptic muscarinic receptors in the forebrain and hippocampus still exist. Therefore muscarinic cholinergic agonists are useful in the treatment of Alzheimer's disease and in improving the cognitive functions of elderly people.

It is well known that arecoline (methyl 1-methyl-1,2,5,6-tetrahydropyridine-3-carboxylate) is such a cholinergic agonist.

Arecoline however has a very short biological half life and a small separation between central and peripheral muscarinic effects. Furthermore arecoline is a rather toxic compound.

Accordingly it is an object of the invention to provide new muscarinic cholinergic compounds.

The novel compounds of the invention of formula I are heterocyclic compounds selected from the group consisting of:

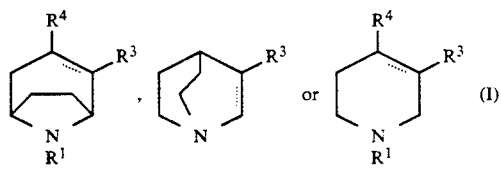

(I)

wherein
$R^1$ is H or $C_{1-6}$-alkyl
$R^3$ is

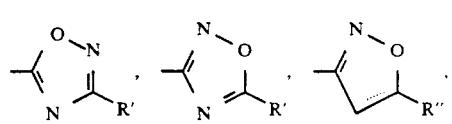

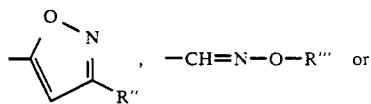

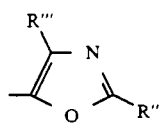

$R^3$ is $C_{3-8}$-alkyl, cyclopropyl, $C_{4-8}$-cycloalkyl, benzyl which may be substituted or $C_{1-4}$-alkoxy-$C_{1-4}$-alkyl, and $R''$ is H or $C_{1-8}$-alkyl or $C_{1-6}$-alkoxy or $C_{1-4}$-alkoxy-$C_{1-4}$-alkyl or aryl, and $R'''$ is H or $C_{1-6}$-alkyl or $C_{4-8}$-cycloalkyl; and $R^4$ is H, $C_{1-8}$-alkyl or Cl;

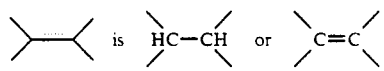

provided that $R^3$ is not

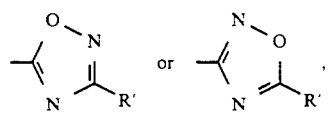

wherein $R'$ is $C_{3-8}$-alkyl, cyclopropyl or $C_{1-3}$-alkoxymethyl, and provided that $R^3$ is not $-CH=N-OR'''$, wherein $R'''$ is H or $C_{1-6}$-alkyl, when the compounds of formula I is

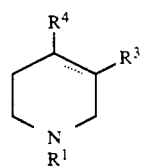

and a salt thereof with a pharmaceutically-acceptable acid.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salt.

The invention also relates to a method of preparing the above mentioned compounds. This method comprises a) reacting a reactive derivative of a compound selected from the group consisting of

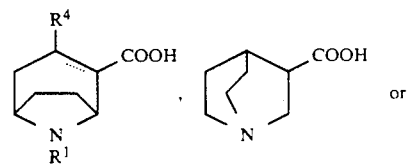

-continued

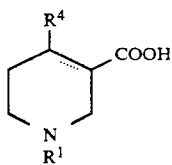

wherein $R^1$, $R^4$ and

have the meanings defined above, with a compound having the formula III $$R'-C(=NOH)NH_2 \qquad (III)$$

wherein R' has the meaning defined above to form a compound of the general formula I, wherein $R^3$ is

wherein R' has the meaning defined above, or b) reacting a compound selected from the group consisting of

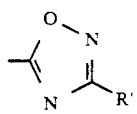

wherein $R^1$, $R^4$ and

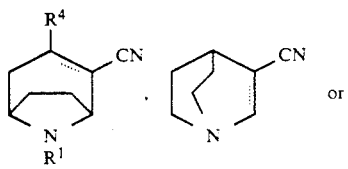

have the meanings defined above, with $NH_2OH$, and reacting the compound thus formed with R'—COCl or $(R'CO)_2O$, wherein R' has the meaning set forth above, to form a compound of formula I, wherein $R^3$ is

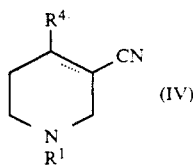

wherein R' has the meaning defined above, or c) reacting a compound selected from the group consisting of

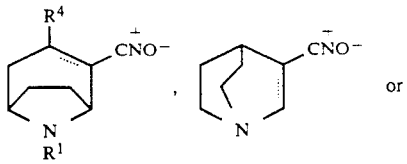

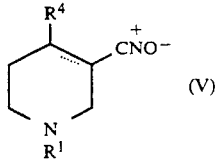

wherein $R^1$, $R^4$ and

have the meanings defined above, with an alkene, alkyne or a equivalent thereof, to form a compound of the general formula I, wherein $R^3$ is

wherein R'' has the meaning defined above, or d) reacting a compound selected from the group consisting of

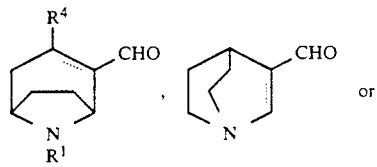

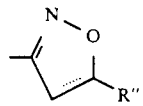

wherein $R^1$, $R^4$ and

have the meanings defined above, with a compound having the formula VII $$NH_2-O-R''' \qquad (VII)$$

wherein R''' has the meaning set forth above, to form a compound of the general formula I, wherein $R^3$ is

—CH=N—O—R''' wherein R''' as the meaning defined above.

e) reacting a compound selected from the group consisting of

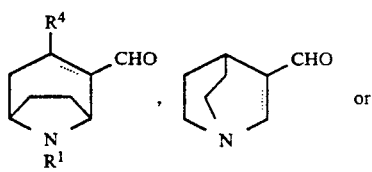

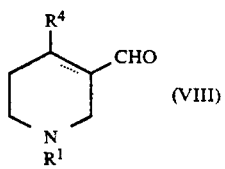 (VIII)

wherein $R^1$, $R^4$ and

have the meanings defined above, with a compound having the formula

wherein R''' has the meaning set forth above to form a compound of the general formula I wherein $R^3$ is

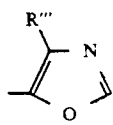

wherein R''' has the meaning defined above.

f) reacting pyridine-3-carbaldehyde with a compound having the formula

wherein R''' has the meaning set forth above, followed by reaction with $R^1$-hal wherein $R^1$ has the meaning defined above, and reacting the compound thus formed with NaBH$_4$ to form a compound of the general formula

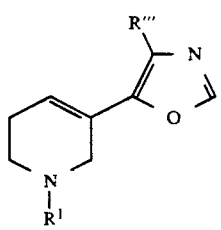

g) reacting 3-acetylpyridine with a compound having the formula

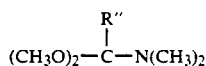

wherein R'' has the meaning set forth above followed by reaction with NH$_2$—OSO$_3$H and $R^1$-hal wherein $R^1$ has the meaning defined above, and reacting the compound thus formed with NaBH$_4$ to form a compound of the general formula

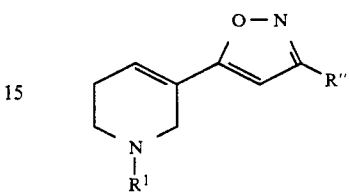

h) reacting 3-ethynylpyridine with a compound having the formula $$R''C\equiv N^+O^-$$

wherein R'' has the meaning set forth above followed by reaction with $R^1$-hal wherein $R^1$ has the meaning defined above, and reacting the compound thus formed with NaBH$_4$ to form a compound of the general formula

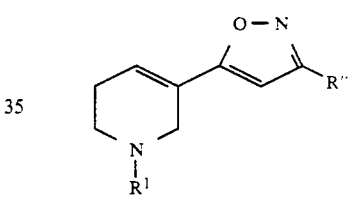

\* \* \* \* \*

The pharmacological properties of the compounds of the invention can be illustrated by determining their capability to inhibit the specific binding of $^3$H-QNB ($^3$H-quinuclidinyl benzilate) by 50%. The inhibitory effect of a substance on $^3$H-QNB binding to brain membranes reflects the affinity of the substance for muscarinic acetylcholine receptors. (Yamamura, H. I. and Snyder, S. H., Proc. Natl. Acad. Sci. 71, 1725–29(1979). The test is carryed out as follows:

Fresh whole forebrain from male Wistar rats (200–250 g) is homogenized by an Ultra-Turrax homogenizer (5–10 s) in volumes of 0.32M sucrose. The homogenate is centrifuged at 4,300×g for 5 min. The pellet is discarded and the supernatant centrifuged at 40,000×g for 15 min. The final pellet is rehomogenized in 50 mM KH$_2$PO$_4$, pH 7.1 (1000 ml per g of original tissue) and this crude membrane preparation is used for binding assays. To 2.5 ml of tissue suspension is added 25 μl of test solution\* and 25 μl $^3$H-QNB (1 nM final concentration). Samples are thoroughly mixed and incubated at 37° C. for 20 min. after incubation, samples are poured directly onto GF/C glass fiber filters under suction and immediately washed 2 times with 10 ml of buffer at 0° C. Non-specific binding is determined in dublicate using atropin (1 μg/ml, final concentration) as the test substance. The amounts of radioactivity on the filters are determined by conventional liquid scintillation counting. Specific binding is total binding minus non-specific binding.

* Test compound is dissolved in 10 ml 96% ethanol (if necessary, acidified by 25 μl 1N HCl and heated on a steambath for less than 5 minutes) at a concentration of 0.22 mg/ml. Three dilutions are made in 48% ethanol (1.1 μg/ml, 11 μg/ml and 110 μg/ml). Concentrations of 10, 100 and 1000 ng/ml (final concentration) are added to duplicate assays. 25-75% inhibition of specific binding must be obtained, before calculation of $IC_{50}$.

The test value will be given as $IC_{50}$ (the concentration/μg/ml) of the test substance which inhibits the specific binding of $^3$H-QNB by 50%).

$$IC_{50} = \text{(applied test substance conc.)} \times \frac{1}{\left[\frac{C_o}{C_x} - 1\right]} \mu g/ml$$

where $C_o$ is specific binding in control assays and $C_x$ is the specific binding in the test assay (the calculation assumes normal mass-action interaction).

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective muscarinic cholinergic agonistic amount of the active ingredient commensurate with the intended daily dosage range to be employed. Tablets containing ten (10) milligrams of the active ingredient or, more broadly, one (1) to hundred (100) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixir of the like can be used in cases where a sweetened vehicle can be employed.

Generally, the compounds of this invention are dispensed in unit form comprising 1-100 mg in a pharmaceutically acceptable carrier per unit dosage.

The dosage of the compounds according to this invention is 1-100 mg/day preferably 10-70 mg/day when administered to patients, e.g. humans, as a drug.

A typical tablet which may be prepared by conventional tabletting techniques contains:

| | |
|---|---|
| Active compound | 5.0 mg |
| Lactosum | 67.8 mg Ph.Eur. |
| Avicel ® | 31.4 mg |
| Amberlite ® IRP 88 | 1.0 mg |
| Magnesii stearas | 0.25 mg Ph.Eur. |

Due to the high muscarinic cholinergic receptor agonistic activity, the compounds of the invention are extremely useful in the treatment symptoms related to a reduction of the cognitive functions of the brain of mammals, when administered in an amount effective for stimulating the cognitive functions of the forebrain and hippocampus. The important stimulating activity of the compounds of the invention includes both activity against the pathophysiological disease, Alzheimer's disease as well as against normal degeneration of brain function. The compounds of the invention may accordingly be administered to a subject, e.g., a living animal body, including a human, in need of stimulation of the cognitive functions of the forebrain and hippocampus, and if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective forebrain and hippocampus stimulating amount, and in any event an amount which is effective for improving the cognitive function of mammals due to their muscarinic cholinergic receptor agonistic activity. Suitable dosage ranges are 1-100 milligrams daily, 10-100 milligrams daily, and especially 30-70 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples:

EXAMPLE 1

2-(3-Cyclopropyl-1,2,4-oxadiazol-5-yl)-8-methyl-8-azabicyclo[3.2.1]oct-2-ene oxalate Sodium (56.6 mg, 2.46 mmol) was dissolved in absolute ethanol (12 ml). Molecular sieves (Type 4A, 1.3 g) and cyclopropancarboxamide oxime (330 mg, 3.30 mmol) were added and the resulting mixture vigorously stirred for 15 min. before addition of cocaine hydrochloride (280 mg, 0.82 mmol). The reaction mixture was heated at 80° for 20 hours. The solution was then filtered from the molecular sieves and the solvent was removed in vacuo. Ether (75 ml) was added to the residue followed by water (20 ml) and the organic phase was separated. The aqueous phase was extracted with ether (2–75 ml), and the combined ether phases were dried (MgSO$_4$, filtered and evaporated.

The title compound was isolated as the oxalate, which was recrystallized from absolute ethanol/ether. M.p. 117° C.

In exactly the same manner the following compound was made:

2-(3-n-butyl-1,2,4-oxadiazol-5-yl)-8-methyl-8-azabicyclo[3.2.1]oct-2-ene oxalate. M.p. 174° C.

EXAMPLE 2

2-(3-Isopropyl-1,2,4-oxadiazol-5-yl)-8-methyl-8-azabicyclo[3.2.1]oct-2-ene oxalate Sodium (303 mg, 13.2 mmol) was dissolved in absolute ethanol (60 ml). Molecular sieves (Type 4A, 7 g) and isopropancarboxamide oxime (2.64 g, 26.4 mmol) were added and the resulting mixture vigorously stirred for 15 min. before addition of cocaine (2.0 g, 6.6 mmol). The reaction mixture was heated at 80° for 24 h and at room temperature for 24 h. The solution was then filtered from the molecular sieves and the solvent was removed in vacuo. Ether (250 ml) was added to the residue followed by water (100 ml) and the organic phase was separated. The aqueous phase was extracted with ether (2×250 ml), and the combined ether phases were dried (MgSO$_4$), filtered and evaporated to give an oil, which was chromatographed on silica gel eluting with ethylacetate and ethanol. The title compound was isolated as the oxalate, which was recrystallized from absolute ethanol/ether. M.p. 162° C.

In exactly the same manner the following compounds were made:

2-(3-Methoxymethyl-1,2,4-oxadiazol-5-yl)-8-methyl-8-azabicyclo[3.2.1]oct-2-ene oxalate M.p. 139° C.

2-(3-(2-Methoxyethyl)-1,2,4-oxadiazol-5-yl)-8-methyl-8-azabicyclo[3.2.1]oct-2-ene oxalate M.p. 165° C.

EXAMPLE 3

2-(3-Cyclopropyl-1,2,4-oxadiazol-5-yl)-8-azabicyclo[3.2.1]oct-2-ene hydrochloride 2-(3-Cyclopropyl-1,2,4-oxadiazol-5-yl)-methyl-8-azabicyclo[3.2.1]oct-2-ene (525 mg, 2.3 mmol) was dissolved in dry dichlorethane (10 ml). The solution was cooled on ice and 1-chloroethyl chloroformate (370 µl, 3.4 mmol was added). The reaction mixture was heated under reflux for 1.5 h and the solvent evaporated. Methanol (20 ml) was added and the mixture heated under reflux for further 1.5 h. The mixture was treated with charcoal, filtered and concentrated in vacuo.

The product was recrystallized from absolute ethanol/ether. M.p. 86° C.

In exactly the same manner the following compounds were made:

2-(3-(2-Methoxyethyl)-1,2,4-oxadiazol-5-yl)-8-azabicyclo[3.2.1]oct-2-ene hydrochloride. M.p. 62 ° C.

2-(3-Isopropyl-1,2,4-oxadiazol-5-yl)-8-azabicyclo[3.2.1]oct-2-ene oxalate, M.p. 168° C.

EXAMPLE 4

3-(3-Cyclopropyl-1,2,4-oxadiazol-5-yl)-2,3-didehydroquinuclidine oxalate

Sodium (181 mg, 7.86 mmol) was dissolved in absolute ethanol (45 ml). Molecular sieves (Type 4A, 5 g) and cyclopropancarboxamide oxime (786 mg, 7.86 mmol) were added and the resulting mixture vigorously stirred for 15 min. before addition of 3-methoxycarbonyl-2,3-didehydroquinuclidine, HCl; prepared as described by Grob et al. in *Helv. Chim. Acta.* (1954), 37, 1689. The reaction mixture was heated at 80° C. for 18 h. The solution was then filtered from the molecular sieves and the solvent was removed in vacuo. Ether (50 ml) was added to the residue followed by water (25 ml) and the organic phase was separated. The aqueous phase was extracted with ether (3×50 ml), and the combined ether phases were dried (Na$_2$SO$_4$) and evaporated to give an oil. This material in dichloromethane (50 ml) was treated for 15 min. at 20° C. with potassium t-butoxide (3 g, 26.79 mmol). After filtration, the material isolated from the filtrate was chromatographed on silica gel eluting with ethylacetate-methanol (3.2:1). The title compound was isolated as the oxalate salt. M.p. 189.0° C.

EXAMPLE 5

3-(3-Isopropyl-1,2,4-oxadiazol-5-yl)-quinuclidine oxalate

Sodium (224 mg, 9.74 mmol) was dissolved in absolute ethanol (45 ml). Molecular sieves (Type 4A, 5 g) and isopropancarboxamide oxime (993 mg, 9.74 mmol) were added and the resulting mixture vigorously stirred for 15 min. before addition of 3-methoxycarbonyl-quinuclidine HCl prepared as described by Grob et al. in *Helv. Chim. Acta.* (1954), 37, 1689. The reaction mixture was heated at 80° C. for 18 h. The solution was then filtered from the molecular sieves and the solvent was removed in vacuo. Ether (50 ml) was added to the residue followed by water (25 ml) and the organic phase was separated. The aqueous phase was extracated with ether (3×50 ml), and the combined ether phases were dried (Na$_2$SO$_4$) and evaporated to afford the title oxadiazole as an oil. The product was further purified as the oxalate salt. M.p. 118°–119°.

In exactly the same manner the following compounds were prepared:

3-(3-butyl-1,2,4-oxadiazol-5-yl)-quinuclidine oxalate, M.p. 122°–124° C.

3-(3-methoxymethyl-1,2,4-oxadiazol-5-yl)-quinuclidine oxalate, M.p. 107°–108° C.

3-(3-cyclopropyl-1,2,4-oxadiazol-5-yl)-quinuclidine oxalate, M.p. 156°–157° C.

EXAMPLE 6

1-Benzoyl-4-chloro-3-formyl-1,2,5,6-tetrahydropyridine oxime

To a solution of 14.6 g (200 mmol) dimethylformamide in 50 ml methylenechloride at 0° C. was added 24.52 g (160 mmol) phosphorus oxychloride at such a rate that the temperature did not exceed 10° C. After addition the reaction mixture was stirred for 1 h at room temperature. The mixture was again cooled to 0° C. and 20.32 g (100 mmol) 1-benzoyl-4-piperidone in 30 ml methylenechloride was added dropwise. After addition (30 min.), the reaction mixture was stirred at room temperature for 2 h whereupon, 150 g crushed ice was added and the mixture stirred until the ice had dissolved. Solid sodium acetate (70 g) was added, and the mixture stirred for 15 min. The methylenechloride fraction was isolated and the aqueous portion was extracted with 2×50 ml methylenechloride. The combined methylenechloride extracts were poured in 100 ml of a saturated sodium bicarbonate solution, and the mixture stirred vigorously for 15 min. The methylenechloride fraction was then isolated, washed with water, dried over magnesium sulfate and concentrated to a volume of 50 ml. To this solution was added 100 ml ethanol, hydroxylamine hydrochloride (6.65 g, 100 mmol) and 15 ml triethylamine. The reaction mixture was stirred overnight, 200 ml water was added and the methylenechloride fraction isolated. The aqueous portion was extracted with 2×50 ml methylenechloride. The combined methylenechloride extracts were dried over magnesiumsulfate, and concentrated in vacuo. To the remaining oil was added 50 ml ethanol and the title compound separated out. Yield: 10.5 g. M.p. 175°–176° C.

In exactly the same manner the following compounds were prepared:

1-Methyl-4-chloro-3-formyl-1,2,5,6-tetrahydropyridine oxime from 1-methyl-4-piperidone and hydroxylamine. M.p. 172°–73° C.

1-Benzyl-4-chloro-3-formyl-1,2,5,6-tetradydropyridine oxime from 1-benzyl-4-piperidone and hydroxylamine M.p. 148°–151° C.

1-Methyl-4-chloro-3-methoxyiminomethyl-1,2,5,6-tetrahydropyridine from 1-methyl-4-piperidone and O-methylhydroxylamine. M.p. 185°–187° C. as oxalate.

8-Ethoxycarbonyl-3-chloro-2-formyl-8-azabicyclo[3.2.1]oct-2-ene oxime from N-(ethoxycarbonyl)nortropan-3-one (G. L. Grunewald et.al. J. Med. Chem. 1988, 31, 433–44). Oil.

EXAMPLE 7

1-Benzoyl-4-chloro-3-(5-methoxymethyl-3-isoxazolyl)-1,2,5,6-tetrahydropyridine

To a solution of 1-benzoyl-4-chloro-3-formyl-1,2,5,6-tetrahydropyridine oxime (5.3 g, 20 mmol) in 100 ml dry dimethylformamide was added N-bromosuccinimide (4.5 g, 25 mmol) dissolved in 20 ml dry dimethylformamide. The reaction mixture was stirred at room temperature for 1 h. Now methylpropargylether (1.5 ml, 25 mmol) and 2 ml triethylamine was added and the reaction mixture stirred at room temperature overnight. 200 ml water was added and the aqueous phase extracted with 3×50 ml ether. The combined ether extracts were washed with 2×50 ml water, dried over magnesiumsulfate and concentrated in vacuo. The compound was finally purified by column chromatography with methylenechloride/ethylacetate 4:1 as eluent. Yield: 3.5 g. M.p. 60.5°–62° C.

In exactly the same manner the following compounds were prepared

1-Benzoyl-4-chloro-3-(5-butyl-3-isoxazolyl)-1,2,5,6-tetrahydropyridine

1-Benzoyl-4-chloro-3-(5-hydroxymethyl-3-isoxazolyl)-1,2,5,6-tetrahydropyridine

1-Benzoyl-4-chloro-3-(5-dimethylaminomethyl-3-isoxazolyl)-1,2,5,6-tetrahydropyridine 1-Benzoyl-4-chloro-3-(5-ethoxy-4,5-dihydro-3-isoxazolyl)-1,2,5,6-tetrahydropyridine 8-Ethoxycarbonyl-3-chloro-2-(5-butyl-3-isoxazolyl)-8-azabicyclo[3.2.1]oct-2-ene 8-Ethoxycarbonyl-3-chloro-2-(5-methoxymethyl-3-isoxazolyl)-8-azabicyclo[3.2.1]oct-2-ene 8-Ethoxycarbonyl-3-chloro-2-(5-phenyl-3-isoxazolyl)-8-azabicyclo[3.2.1]oxt-2-ene 1-Benzoyl-4-chloro-3-(5-methyl-3-isoxazolyl)-1,2,5,6-tetrahydropyridine To a solution of 1-benzoyl-4-chloro-3-formyl-1,2,5,6-tetrahydropyridine oxime (5,3 g, 20 mmol) in 100 ml dry dimethylformamide was added N-bromosuccinimide (4.5 g, 25 mmol) dissolved in 20 ml dry dimethylformamide. The reaction mixture was stirred at room temperature for 1 h. Now 2-bromopropene (2.2 ml, 25 mmol) and 4 ml triethylamine were added and the reaction mixture stirred at room temperature for 48 h. The compound was purified as described for 1-Benzoyl-4-chloro-3-(5-methoxymethyl-3-isoxazolyl)-1,2,5,6-tetrahydropyridine. Yield: 3.1 g. M.p. 86°–87° C.

In exactly the same manner the following compound was prepared

8-Ethoxycarbonyl-3-chloro-2-(5-methyl-3-isoxazolyl)-8-azabicyclo[3.2.1]oct-2-ene

EXAMPLE 8

4-Chloro-3-(5-methoxymethyl-3-isoxazolyl)-1,2,5,6-tetrahydropyridine oxalate

A suspension of 1.65 g (5 mmol) of 1-benzoyl-4-chloro-3-(5-methoxymethyl-3-isoxazolyl)-1,2,5,6-tetrahydropyridine in 30 ml 6M hydrochloric acid solution was heated at reflux for 5 h. After cooling to room temperature 30 ml water was added and the aqueous phase extracted with 2×30 ml ether. The aqueous phase was made strongly alkaline with solid potassiumcarbonate and extracted with 2×30 ml ether. The combined ether extracts were dried over magnesiumsulfate and concentrated in vacuo. The remaining oil was dissolved in 10 ml acetone, and the title compound was precipitated with a 1M oxalic acid acetone solution. The compound was filtered and dried. Yield: 0.65 g. M.p. 155°–156° C.

In exactly the same manner the following compounds were prepared

4-Chloro-3-(5-methyl-3-isoxazolyl)-1,2,5,6-tetrahydropyridine oxalate starting from 1-benzoyl-4-chloro-3-(5-methyl-3-isoxazolyl)-1,2,5,6-tetrahydropyridine. M.p. 180°–181° C.

4-Chloro-3-(5-butyl-3-isoxazolyl)-1,2,5,6-tetrahydropyridine oxalate starting from 1-benzoyl-4-chloro-3-(5-butyl-3-isoxazolyl)-1,2,5,6-tetrahydropyridine. M.p. 164°–165° C.

4-Chloro-3-(5-hydroxymethyl-3-isoxazolyl)-1,2,5,6-tetrahydropyridine oxalate starting from 1-benzoyl-4-chloro-3-(5-hydroxymethyl-3-isoxazolyl)-1,2,5,6-tetrahydropyridine. M.p. 167°–169° C.

4-Chloro-3-(5-dimethylaminomethyl-3-isoxazolyl)-1,2,5,6-tetrahydropyridine oxalate starting from 1-benzoyl-4-chloro-3-(5-dimethylaminomethyl-3-isoxazolyl)-1,2,5,6-tetrahydropyridine. M.p. 226°–29° C.

4-Chloro-3-(3-isoxazolyl)-1,2,5,6-tetrahydropyridine oxalate starting from 1-benzoyl-4-chloro-3-(5-ethoxy-4,5-dihydro-3-isoxazolyl)-1,2,5,6-tetrahydropyridine. M.p. 195°–196° C.

EXAMPLE 9

3-(5-Methoxymethyl-3-isoxazolyl)-1 2 5.6-tetrahydropyridine oxalate

1-Benzoyl-4-chloro-3-(5-methoxymethyl-3-isoxazolyl)-1,2,5,6-tetrahydropyridine (0.8 g, 2.5 mmol) was dissolved in 50 ml ethanol. To this solution was added a suspension of palladium-on-charcoal (5%, 0.5 g) in 10 ml ethanol and 2 ml triethylamine. The mixture was reduced with hydrogen at atmospheric pressure until exactly 1.2 equivalent of hydrogen was consumed. The catalyst was filtered off and the solution concentrated in vacuo. The remaining oil was suspended in 20 ml 6M hydrochloric acid solution and heated at reflux for 5 h. After cooling 20 ml water was added and the aqueous solution was extracted with 2×20 ml ether. The aqueous solution was made strongly alkaline with solid potassium carbonate and extracted with 3×20 ml methylenechloride. The combined methylenechloride extracts were dried over magnesiumsulfate and concentrated in vacuo. The remaining oil was dissolved in 10 ml acetone, and the title compound was precipitated with a 1M oxalic acid acetone solution. The compound was filtered and dried. Yield: 0.2 g. M.p. 152°-153° C.

In exactly the same manner the following compounds were prepared:

3-(5-methyl-3-isoxazolyl)-1,2,5,6-tetrahydropyridine oxalate starting from 1-benzoyl-4-chloro-3-(5-methyl-3-isoxazolyl)-1,2,5,6-tetrahydropyridine. M.p. 176°-177° C.

3-(5-Butyl-3-isoxazolyl)-1,2,5,6-tetrahydropyridine oxalate starting from 1-benzoyl-4-chloro-3-(5-butyl-3-isoxazolyl)-1,2,5,6-tetrahydropyridine. M.p. 188°-91° C.

EXAMPLE 10

3-(5-Propyl-1,2,4-oxadiazol-3-yl)-2,3-didehydroquinuclidine oxalate

To a solution of sodium (575 mg, 25 mmol) in methanol (20 ml) was added a solution of hydroxylamine hydrochloride (1.55 g, 22 mmol) in methanol (20 ml). The mixture was stirred for 30 min, and filtrated. To the filtrate a solution of 3-cyano-2,3-didehydroquinuclidine (Helv. Chem. Acta 40, 2170 (1957)) (1.2 g, 9 mmol) in methanol (5 ml) was added and the reaction mixture was stirred at room temperature for 48 h. After evaporation the residue was suspended in absolute ethanol (25 ml), filtered and evaporated to give the 2,3-didehydroquinuclidineamide oxime. The amide oxime (700 mg) was dissolved in butyric anhydride and stirred at 100° C. for 16 h. After evaporation the residue was dissolved in a saturated potassium carbonate solution (10 ml) and extracted with ether (3×75 ml). The combined organic phases were dried and evaporated. The residue was purified (column chromatography with 1,2-dichloroethane-methanol (9:1) as eluent). Crystallization as the oxalate salt from acetone gave the title compound in a 300 mg yield. M.p. 155°-157° C.

3-(5-Cyclopropyl-1,2,4-oxadiazol-3-yl)-2,3-didehydroquinuclidine oxalate

This compound was synthesized as described above using cyclopropanecarboxylic acid chloride followed by cyclization in refluxing toluene instead of butyric anhydride. M.p. 170-°172° C.

8-Methyl-2-(5-propyl-1,2,4-oxadiazol-3-yl)-8-azabicyclo[3.2.1]oct-2-ene oxalate This compound was synthesized as described above starting from 2-cyano-8-methyl-8-azabicyclo[3.2.1]oct-2-ene [J. C. S. Perkin I, 1981, 1346°-1351]. M.p. 99°-101° C.

EXAMPLE 11

3-(5-Oxazolyl)-1,2,5,6-tetrahydro-1-methylpyridine oxalate

To a solution of 1-methyl-3-formyl-1,2,5,6-tetrahydropyridine hydrochloride (Mannich Berichte 75, 1480-83, 1942) 1.60 g, 10 mmol) in 20 ml methanol powdered potassium carbonate (3 g) was added. Then tosylmethylisocyanide (1.95 g, 10 mmol) was added and the reaction mixture stirred at room temperature for 2 h. Upon evaporation in vacuo, water (30 ml) was added to the residue, and the solution was extracted with methylenechloride 3×20 ml. The combined methylenechloride extracts were dried over magnesiumsulfate and evaporated in vacuo. The crude compound was purified by column chromatography with acetone as eluent. The title compound was precipitated with a 1M oxalic acid acetone solution, filtered and dried. M.p. 169°-170° C.

1-Methyl-3-(4-propyl-5-oxazolyl)-1,2,5,6-tetrahydropyridine oxalate

A mixture of 1.07 g (10 mmol) pyridin-3-carbaldehyde 2.61 g (11 mmol) 1-tosyl-1-isocyanobutane and powdered potassium carbonate in methanol (50 ml) was stirred for 12 h at room temperature. The reaction mixture was concentrated in vacuo and water (100 ml) was added. The water suspension was extracted with 3×30 ml ethylacetate. The organic phase was dried over magnesiumsulfate and concentrated in vacuo. The residue was dissolved in 50 ml acetone and 3.12 g (22 mmol) methyliodide was added. The reaction mixture was stirred overnight at room temperature, concentrated in vacuo and titurated with ethylacetate. The precipitated crystals were dissolved in ethanol (50 ml) and treated with 1.06 g (28 mmol) sodiumborohydride. The mixture was concentrated in vacuo and water (100 ml) was added. The water suspension was extracted with 3×30 ml methylenchloride. The organic phase was dried over magnesium sulfate and concentrated in vacuo. The compound was purified by column chromatographay with ethylacetate/methanol (9:1) as eluent. Crystallization as the oxalate salt from acetone gave the title compound in a 940 mg yield. M.p. 100°-101° C.

EXAMPLE 12

3-(Cyclopropylmethoxyiminomethyl)-1 2 5.6-tetrahydro-1-methylpyridine oxalate To a solution of 1-methyl-3-formyl-1,2,5,6-tetrahydropyridine hydrochloride (Mannich Berichte 75, 1480-83, 1942) (1.60 g, 10 mmol) in 20 ml ethanol cyclopropylmethoxyamine hydrochloride (1.24 g, 10 mmol) and triethylamine (3 ml) were added. The reaction mixture was stirred at room temperature for 1 h, then evaporated in vacuo. 30 ml sodium hydroxide solution (0.5M) was added to the residue, and the solution was extracted with methylenechloride (3×20 ml). The combined methylenechloride extracts were dried and evaporated in vacuo. The residue was dissolved in acetone and the title compound was precipitated with a 1M oxalic acid acetone solution. The compound was filtered and dried. M.p. 143°–144° C.

EXAMPLE 13

3-Chloro-2-formyl-8-methyl-8-azabicyclo[3.2.1]oct-2-ene oxalate

To a dimethylformamide (4.5 ml, 60 mmol) at 0° C. was added phosphorous oxychloride (3 ml, 30 mmol). Tropinone (2 g, 13 mmol) was added, and the reaction mixture heated to 70° C. for ½ h After cooling, crushed ice was added and then solid potassium carbonate until alkaline reaction. The water solution was extracted with ether (3×30 ml). The ether extracts were dried and evaporated. The crude compound was purified by column chromatography with acetone as eluent. The title compound was precipitated with a 1M oxalic acid acetone solution, filtered and dried. M.p. 136°–137° C. decomposes.

EXAMPLE 14

3-Chloro-2-(cyclopropylmethoxyiminomethyl)-8-methyl-8-azabicyclo[3.2.1]oct-2-ene oxalate To a solution of 3-chloro-2-formyl-8-methyl-8-azabicyclo[3.2.1]oct-2-ene oxalate (0.55 g, 2 mmol) in 20 ml ethanol cyclopropylmethoxyamine hydrochloride (0.25 g, 2 mmol) and triethylamine (1 ml) was added. The reaction mixture was stirred at room temperature for 1 h, then evaporated in vacuo. 20 ml sodiumhydroxide solution (0.5M) was added to the residue, and the solution was extracted with methylenechloride (3×15 ml). The combined methylenechloride extracts were dried and evaporated in vacuo. The residue was dissolved in acetone (10 ml) and the title compound was precipitated with a 1M oxalic acid acetone solution. The compound was filtered and dried M.p 170°–171° C.

In exactly the same manner the following compound was prepared:

3-Chloro-2-(methoxyiminomethyl)-8-methyl-8-azabicyclo[3.2.1]oct-2-ene oxalate from 3-chloro-2-formyl-8-methyl-8-azabicyclo[3.2.1]oct-2-ene oxalate and methoxyamine hydrochloride, M.p. 180°–185° C.

EXAMPLE 15

3-Chloro-8-methyl-2-(5-oxazolyl)-8-azabicyclo[3.2.1]oct-2-ene oxalate

To a solution of 3-chloro-2-formyl-8-methyl-8-azabicyclo[3.2.1]oct-2-ene oxalate (0.55 g, 2 mmol) in 20 ml methanol powdered potassium carbonate (1.5 g) and tosylmethylisocyanide (0.4 g, 2 mmol) was added. The reaction mixture was stirred at room temperature for 2 h. Upon evaporation in vacuo water (30 ml) was added to the residue and the water solution extracted with methylenechloride (3×20 ml). The combined methylenechloride extracts were dried and evaporated in vacuo. The residue was dissolved in ethanol, and the title compound precipitated with a 1M oxalic acid ether solution. The compound was filtered and dried. M.p. 69°–71° C. decomposes.

EXAMPLE 16

2-Methoxyiminomethyl-8-methyl-8-azabicyclo[3.2.1]oct-2-ene oxalate

To a solution of 2-formyl-8-methyl-8-azabicyclo[3.2.1]oct-2-ene (T. Bacesov and M. Shives, J. Am. Chem. Soc., 107, 7524–33, 1985) (0.3 g, 2 mmol) in 20 ml ethanol methoxyamine hydrochloride (0.17 g, 2 mmol) and triethylamine 0.5 ml was added. The reaction mixture was stirred at room temperature for 1 h, then evaporated in vacuo. Sodiumhydroxide solution (20 ml, 0.5 mmol) was added to the residue and the solution was extracted with methylenechloride (3×15 ml). The combined methylenechloride extracts were dried and evaporated in vacuo. The residue was dissolved in acetone (5 ml) and the title compound was precipitated with a 1M oxalic acid acetone solution. The compound was filtered and dried. M.p. 129°–130° C.

In exactly the same manner the following compound was prepared:

2-Ethoxyiminomethyl-8-methyl-8-azabicyclo[3.2.1]oct-2-ene oxalate from 2-formyl-8-methyl-8-azabicyclo[3.2.1]oct-2-ene and ethoxyamine hydrochloride. M.p. 127°–128° C.

EXAMPLE 17

3-(3-Cyclobutyl-1,2,4-oxadiazol-5-yl)-1-methyl-1,2,5,6-tetrahydropyridine oxalate To a solution of sodium ethoxide (prepared from sodium (34 mg, 1.48 mmol), destilled ethanol (20 ml) and molecular sieves (4 g) was added cyclobutancarboxamide oxime (169 mg, 1.48 mmol). The mixture was stirred at room temperature for 10 min. and arecoline, hydrobromide (175 mg, 0.74 mmol) was added. The reaction mixture was stirred at 80° C. for 18 h, filtered and evaporated. Water (10 ml) was added to the residue, and the solution was extracted with ether (3×30 ml). The combined ether phases were dried and evaporated to give the crude product as an oil. Crystallization as the oxalate salt from absolute ethanol gave the title compound in a yield of 60 mg. M.p. 148°–149° C.

In exactly the same manner the following compounds were prepared:

3-(3-cyclopentyl-1,2,4-oxadiazol-5-yl)-1-methyl-1,2,5,6-tetrahydropyridine oxalate. M.p. 132°–133° C.

3-(3-(2-methoxyethyl)-1,2,4-oxadiazol-5-yl)-1-methyl-1,2,5,6-tetrahydropyridine oxalate. M.p. 140°–141° C.

3-(3-(2-ethoxyethyl)-1,2,4-oxadiazol-5-yl)-1-methyl-1,2,5,6-tetrahydropyridine oxalate. M.p. 143°–144° C.

3-(3-(2-methoxybenzyl)-1,2,4-oxadiazol-5-yl)-1-methyl-1,2,5,6-tetrahydropyridine oxalate. M.p. 76°–77° C.

Using norarecoline instead of arecoline the following compounds were made in exactly the same manner as described above:

3-(3-cyclobutyl-1,2,4-oxadiazol-5-yl)-1,2,5,6-tetrahydropyridine oxalate. M.p. 202°–205° C.

3-(3-cyclopentyl-1,2,4-oxadiazol-5-yl)-1,2,5,6-tetrahydropyridine oxalate. M.p. 152°–158° C.

EXAMPLE 18

3-(5-Isoxazolyl)-1-methyl-1,2,5,6-tetrahydropyridine oxalate

A mixture of 12.1 g (0.1 mol) 3-acetyl pyridine and 15 g (0.11 mol) dimethyl formamide dimethylacetale was heated at 90° C. for 2 h. Upon concentration in vacuo the product was titrated with ethylether and filtrated. The compound was dissolved in 50 ml methanol and 11.5 g (0.1 mol) hydroxylamine-O-sulfonic acid dissolved in 50 ml MeOH was added. The reaction mixture was stirred at room temperature for 2 h, concentrated in vacuo and poured on water (150 ml). The solution was made alkaline with solid potassium carbonate and extracted with 4×40 ml methylenchloride. The organic phase was dried over magnesium sulfate and concentrated in vacuo. The crude product was purified by column chromatography giving 1.5 g 3-(5-isoxazolyl)-pyridine, which was dissolved in 20 ml acetone. 3 ml methyliodide was added to the solution, and the reaction mixture was stirred at room temperature for 24 h. The precipitated compound was filtered and dissolved in 30 ml methanol. To this solution sodiumborohydride (600 mg) was added in small portions. The reaction mixture was concentrated in vacuo and water (100 ml) was added. The water solution was extracted with 3×30 ml methylenchloride. The organic phase was dried over magnesiumsulfate and concentrated in vacuo. Crystallization as the oxalate salt from acetone gave the title compound in a 1.1 g yield. M.p. 164°–165° C.

3-(3-Methyl-5-isoxazolyl)-1,2,5,6-tetrahydropyridine oxalate

This compound was prepared as described above starting from 3-acetylpyridine and dimethylacetamide dimethylacetale. M.p. 167°–169° C.

3-(3-Ethyl-5-isoxazolyl)-1-methyl-1,2,5,6-tetrahydropyridine oxalate 0.45 g (5 mmole) nitropropane and 5 ml 1N (5 mmole) sodiummethoxide was dissolved in dry dimethylacetamide (25 ml). To this solution 0.39 g (5 mmole) acetylchloride and 0.51 g (5 mmole) 2-ethynylpyridine was added. The reaction mixture was stirred overnight at room temperature. Water (150 ml) was added, and the solution extracted with 3×30 ml ethylacetate. The organic phase was dried over magnesiumsulphate and concentrated in vacuo giving 3-(3-ethyl-5-isoxazolyl)-pyridine in a 500 mg yield. This compound was quartarnized with methyliodide and reduced with sodiumborohydride as described above giving the title compound in a 170 mg yield. M.p. 169°–170° C.

EXAMPLE 19

3-(3-Cyclopropyl-1,2,4-oxadiazol-5-yl)-1,4-dimethyl-1,2,5,6-tetrahydropyridine oxalate Sodium (54.4 mg, 2.37 mmol) was dissolved in absolute ethanol (10 ml). Molecular sieves (Type 4 Å, 1 g) and cyclopropanylcarboxamide oxime (236 mg, 2.37 mmol) were added and the resulting mixture vigorously stirred for 15 min. before addition of 1,4-dimethyl-3-methoxycarbonyl-1,2,5,6-tetrahydropyridine oxalate (200 mg, 1.18 mmol). The reaction mixture was heated at 80° C. for 18 h. The solution was then filtered from the molecular sieves and the solvent was removed in vacuo. Ether (40 ml) was added to the residue followed by water (15 ml) and the organic phase was separated. The aqueous phase was extracted with ether (3×40 ml), and the combined ether phases were dried (Na$_2$SO$_4$) and evaporated to afford the title oxadiazole as an oil. The product was further purified as the oxalate salt. M.p. 152°–153° C.

In exactly the same manner the following compound was prepared:
3-(3-Butyl-1,2,4-oxadiazol-5-yl)-1,4-dimethyl-1,2,5,6-tetrahydropyridine oxalate. M.p. 147°–148° C.

EXAMPLE 20

3-Chloro-2-(5-butyl-3-isoxazolyl)-8-azabicyclo[3.2.1]oct-2-ene oxalate

To a solution of 1.0 g (3 mmol) of 8-ethoxycarbonyl-3-chloro-2-(5-butyl-3-isoxazolyl)-8-azabicyclo[3.2.1]oct-2-ene in dry toluene (20 ml), 2 g (15 mmol) aluminiumtrichloride was added. The reaction mixture was heated at 70° C. for 15 min., then cooled and poured on ice water (100 ml). The phases were separated and the water phase extracted with 2×20 ml ethylether. The water phase was made alkaline With a sodiumhydroxide solution (2 N), and extracted with 3×30 ml methylenchloride. The organic phase was dried over magnesiumsulphate and concentrated in vacuo. Crystallization as the oxalate salt from acetone gave the title compound in a 450 mg yield. M.p. 112°–114° C.

In exactly the same manner the following compounds were prepared:
3-Chloro-2-(5-methoxymethyl-3-isoxazolyl)-8-azabicyclo[3.2.1]oct-2-ene oxalate. M.p. 153°–154° C.
3-Chloro-2-(5-phenyl-3-isoxazolyl)-8-azabicyclo[3.2.1]oct-2-ene oxalate. M.p. 135°–136° C.
3-Chloro-2-(5-methyl-3-isoxazolyl)-8-azabicyclo[3.2.1]oct-2-ene oxalate. M.p. 136°–137° C.
2-(5-phenyl-3-isoxazolyl)-8-azabicyclo[3.2.1]oct-2-ene oxalate. M.p. 163°–164° C.

EXAMPLE 21

8-Ethoxycarbonyl-2-(5-phenyl-3-isoxazolyl)-8-azabicyclo[3.2.1]oct-2-ene 1.3 g (3.6 mmol) 8-ethoxycarbonyl-3-chloro-2-(5-phenyl-3-isoxazolyl)-8-azabicyclo[3.2.1]oct-2-ene was dissolved in 30 ml ethanol. 300 mg Pd/C 5%, triethylamine (7 ml) and formic acid (3 ml) was added and the reaction mixture heated at reflux for 4 h. The mixture was concentrated in vacuo, water (50 ml) was added and the solution extracted with ethylether 3×20 ml. The organic phase was dried over magnesiumsulphate and concentrated in vacuo. The crude product was purified by column chromatography with methylenchloride/ethylacetate (9:1) as eluent. Yield 600 mg oil.

EXAMPLE 22

4-Chloro-3-(5-methoxymethyl-3-isoxazolyl)-1-methyl-1,2,5,6-tetrahydropyridine oxalate To a mixture of formic acid (5 ml) and formaldehyde 37% (10 ml) 1.6 g (5 mmole) 4-chloro-3-(5-methoxymethyl-3-isoxazolyl)-1,2,5,6-tetrahydropyridine oxalate was added. The reaction mixture was heated at reflux for 1 h. After cooling the reaction mixture was poured on water (50 ml) and made alkaline with solid potassiumcarbonate. The water phase was extracted with 3×30 ml methylenchloride. The organic phases were dried over magnesiumsulphate and concentrated in vacuo. Crystallization as the oxalate salt from acetone gave the title compound in a 1.25 g yield. M.p. 171°–172° C.

In exactly the same manner the following compounds were prepared:
3-Chloro-8-methyl-2-(5-methyl-3-isoxazolyl)-8-azabicyclo[3.2.1]oct-2-ene oxalate with 3-chloro-2-(5-methyl-3-isoxazolyl)-8-azabicyclo[3.2.1]oct-2-ene oxalate as starting compound. M.p. 149°–150° C.
3-Chloro-8-methyl-2-(5-phenyl-3-isoxazolyl)-8-azabicyclo[3.2.1]oct-2-ene oxalate with 3-chloro-2-(5-phenyl-3-isoxazolyl)-8-azabicyclo[3.2.1]oct-2-ene oxalate as starting compound. M.p. 260°–261° C.

We claim:
1. A compound of formula I

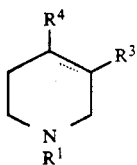

wherein p1 R$^1$ is H or C$_{1-6}$-alkyl;
R$^3$ is

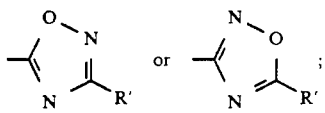

wherein
R' is benzyl or methoxybenzyl;
R$^4$ is H, C$_{1-8}$-alkyl or Cl; and

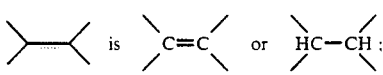

or a pharmaceutically acceptable salt thereof.

2. The compound according to claim 1, wherein R$^1$ is H or methyl and R$^4$ is H or methyl.

3. The compound according to claim 2 which is 3-(3-(2-methoxybenzyl)-1,2,4-oxadiazol-5-yl)-1-methyl-1,2,5,6-tetrahydropyridine or a pharmaceutically acceptable salt thereof.

4. A compound of formula II

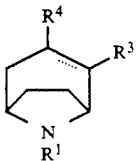

wherein
R$^1$ is H or C$_{1-6}$-alkyl;
R$^3$ is

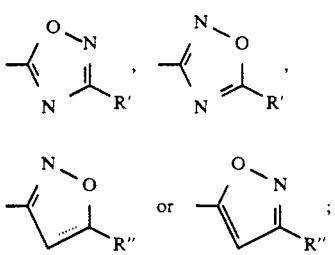

wherein
R' is C$_{3-8}$-cycloalkyl, benzyl or methoxybenzyl and
R" is H, C$_{1-8}$-alkyl, C$_{1-6}$-alkoxy, C$_{1-4}$-alkoxy-C$_{1-4}$-alkyl or phenyl;
R$^4$ is H, C$_{1-8}$-alkyl or Cl; and

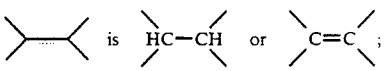

or a pharmaceutically acceptable salt thereof.

5. The compound according to claim 4, wherein R$^1$ is H or methyl and R$^4$ is H or methyl.

6. The compound according to claim 5 which is 2-(3-cyclopropyl-1,2,4-oxadiazol-5-yl)-8-methyl-8-azabicyclo[3.2.1]oct-2-ene or a pharmaceutically acceptable salt thereof.

7. The compound according to claim 5 which is 3-chloro-2-(5-butyl-3-isoxazolyl)-8-azabicyclo[3.2.1]oct-2-ene or a pharmaceutically acceptable salt thereof.

8. The compound according to claim 5 which is 3-chloro-2-(5-methoxymethyl-3-isoxazolyl)-8-azabicyclo[3.2.1]oct-2-ene or a pharmaceutically acceptable salt thereof.

9. The compound according to claim 5 which is 3-chloro-2-(5-methyl-3-isoxazolyl)-8-azabicyclo[3.2.1]oct-2-ene or a pharmaceutically acceptable salt thereof.

10. The compound according to claim 5 which is 3-chloro-8-methyl-2-(5-methyl-3-isoxazolyl)-8-azabicyclo[3.2.1]oct-2-ene or a pharmaceutically acceptable salt thereof.

11. The compound according to claim 5 which is 2-(3-cyclopropyl-1,2,4-oxadiazol-5-yl)-8-azabicyclo[3.2.1oct-2-ene or a pharmaceutically acceptable salt thereof.

12. The compound according to claim 5 which is 3-chloro-2-(5-phenyl-3-isoxazolyl)-8-azabicyclo[3.2.1oct-2-ene or a pharmaceutically acceptable salt thereof.

13. The compound according to claim 5 which is 2-(5-phenyl-3-isoxazolyl)-8-azabicyclo[3.2.1]oct-2-ene or a pharmaceutically acceptable salt thereof.

14. The compound according to claim 5 which is 3-chloro-8-methyl-2-(5-phenyl-3-isoxazolyl)-8-azabicyclo[3.2.1oct-2-ene or a pharmaceutically acceptable salt thereof.

15. A compound of formula III

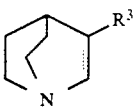

wherein
R$^3$ is

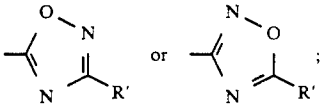

wherein
R' is C$_{3-8}$-cycloalkyl, benzyl or methoxybenzyl; and

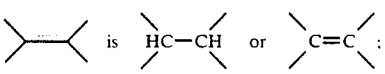

or a pharmaceutically acceptable salt thereof.

16. The compound according to claim 15 which is 3-(3-cyclopropyl-1,2,4-oxadiazol-5-yl)-2,3-didehydroquinuclidine or a pharmaceutically acceptable salt thereof.

17. The compound according to claim 15 which is 3-(3-cyclopropyl-1,2,4-oxadiazol-5-yl)-quinuclidine or a pharmaceutically acceptable salt thereof.

18. The compound according to claim 15 which is 3-(5-cyclopropyl-1,2,4-oxadiazol-3-yl)-2,3-didehydroquinuclidine or a pharmaceutically acceptable salt thereof.

19. A pharmaceutical composition suitable for use in treating Alzheimer's disease, comprising an effective amount of a compound according to claim 1, 4 or 15 together with a pharmaceutically acceptable carrier or diluent.

20. The pharmaceutical composition according to claim 19 in the form of an oral dosage unit containing 1-100 mg of the active compound.

21. A method for treating Alzheimer's disease comprising administering to a subject in need thereof an effective amount of a compound according to claim 1, 4 or 15.

22. A method for treating Alzheimer's disease, comprising administering to a subject in need thereof a pharmaceutical composition according to claim 19.

* * * * *